(12) United States Patent
Winckle et al.

(10) Patent No.: US 8,486,978 B2
(45) Date of Patent: *Jul. 16, 2013

(54) COMPOSITIONS AND METHODS FOR TREATING DISEASES OF THE NAIL

(75) Inventors: Gareth Winckle, Petaluma, CA (US); Gregory T. Fieldson, Morgantown, WV (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 108 days.

This patent is subject to a terminal disclaimer.

(21) Appl. No.: 13/199,717

(22) Filed: Sep. 7, 2011

(65) Prior Publication Data

US 2012/0010246 A1    Jan. 12, 2012

Related U.S. Application Data

(63) Continuation of application No. 12/803,848, filed on Jul. 8, 2010, now Pat. No. 8,039,494.

(51) Int. Cl.
*A01N 43/64* (2006.01)
*A61K 31/41* (2006.01)

(52) U.S. Cl.
USPC .......................................... 514/359; 514/383

(58) Field of Classification Search
None
See application file for complete search history.

(56) References Cited

U.S. PATENT DOCUMENTS

| | | | |
|---|---|---|---|
| 4,457,938 A | 7/1984 | von Bittera | |
| 4,912,124 A | 3/1990 | Das | |
| 5,461,068 A | 10/1995 | Thaler | |
| 5,696,105 A | 12/1997 | Hackler | |
| 5,814,305 A | 9/1998 | Laugier | |
| 6,197,305 B1 | 3/2001 | Friedman | |
| 6,231,875 B1 | 5/2001 | Sun | |
| 6,538,039 B2 | 3/2003 | Laurent | |
| 6,585,963 B1 | 7/2003 | Quan | |
| 6,676,953 B2 | 1/2004 | Hexamer | |
| 6,740,326 B1 | 5/2004 | Meyer | |
| 6,846,837 B2 | 1/2005 | Maibach | |
| 7,214,506 B2 | 5/2007 | Tatsumi | |
| 2003/0007939 A1 | 1/2003 | Murad | |
| 2003/0082129 A1 | 5/2003 | Buckingham | |
| 2004/0180025 A1 | 9/2004 | Long | |
| 2005/0186161 A1* | 8/2005 | Kawase et al. | 424/61 |
| 2005/0244342 A1 | 11/2005 | Friedman | |
| 2006/0110415 A1 | 5/2006 | Gupta | |
| 2006/0147383 A1 | 7/2006 | Mallard | |
| 2007/0041910 A1 | 2/2007 | Pitre | |
| 2007/0071705 A1* | 3/2007 | De Oliveira et al. | 424/70.13 |
| 2007/0082375 A1 | 4/2007 | Tatsumi | |
| 2009/0175810 A1 | 7/2009 | Winckle | |

FOREIGN PATENT DOCUMENTS

| | | |
|---|---|---|
| GB | 2407496 | 10/2003 |
| WO | WO 87/02580 | 5/1987 |
| WO | WO 99/49835 | 10/1999 |

OTHER PUBLICATIONS

Tatsumi et al., Therapeutic efficacy of topically applied KP-103 against experimental Tinea Unguim in Guinea Pigs in comparison with amorolfine and Terbinafine, Antimicrobial Agents and Chemotherapy, 46 (12), 3797-3801.*

Tatsumi et al., Therapeutic efficacy of topically applied KP-103 against experimental Tinea Unguim in Guinea Pigs in comparison with amorolfine and Terbinafine, Antimicrobial Agents and Chemotherapy, 46 (12), 3797-3801, 2002.*

Tatsumi Y, et al, "Therapeutic Efficacy of Topically Applied KP-103 against Experimental Tinea Urguium . . ." Antimicrobial Agents and Chemotherapy, 46(12):3797-3801 (2002).

Jannsen Pharmaceuticals, "Pevaryl®" (2009).

Vanderdonckt, Mykosen, 19(17):251-256 (1976).

* cited by examiner

*Primary Examiner* — Sreeni Padmanabhan
*Assistant Examiner* — Svetlana M Ivanova
(74) *Attorney, Agent, or Firm* — Howard Eisenberg, Esq.; Len S. Smith

(57) ABSTRACT

Methods and compositions for treating disorders of the nail and nail bed. Such compositions contain a vehicle in which all components of the composition are dissolved, suspended, dispersed, or emulsified, a non-volatile solvent, a wetting agent, and a pharmaceutically active ingredient that is soluble in the non-volatile solvent and/or a mixture of the vehicle and the non-volatile solvent, which composition has a surface tension of 40 dynes/cm or less and has continuing spreadability, and which composition is effective in treating a disorder of the nail or nail bed.

42 Claims, 3 Drawing Sheets

COMPOSITIONS AND METHODS FOR TREATING DISEASES OF THE NAIL

This application claims priority of pending U.S. patent application Ser. No. 12/803,848, filed Jul. 8, 2010.

FIELD OF THE INVENTION

The invention pertains to the field of treatment of diseases of the nail and nail bed. In particular, the invention pertains to methods for treatment of disorders such as onychomycosis or psoriasis involving the nails.

BACKGROUND OF THE INVENTION

Onychomycosis, a fungal disease of the nail unit caused by yeasts, dermatophytes, or other molds, accounts for approximately 50% of all nail disorders in humans. In about 80% of onychomycosis cases, the toenails are infected, whereas in the remaining 20%, the fingernails are infected. The signs and symptoms of this disease include split, thickened, hardened, and rough nail plates, and partial separation of the nail plate from the nail bed creating an air gap in some areas.

Another common disorder of nails is nail psoriasis, which affects up to 50% of patients with psoriasis. Characteristic nail psoriasis symptoms include pitting, which appears as punctuated or irregularly shaped depressions arranged on the surface of the body of the nail; discoloration of the nail bed; onycholysis or detachment of the body of the nail from the nail bed; subungual keratosis; or anomalies of the body of the nail. Other diseases and disorders involving the nails in humans and in other animals include onychia, onychocryptosis, onychodystrophy, onychogryposis, onycholysis, onychomadesis, onychophosis, onychoptosis, paronychia, koilonychia, subungual hematoma, and laminitis.

The nail plate is thick, hard, and dense, and represents a formidable barrier to drug penetration. Although nail material is similar in various ways to the stratum corneum of the skin, the nail is composed primarily of hard keratin which is highly disulfide-linked and is approximately 100-fold thicker than stratum corneum. In certain nail diseases, such as onychomycosis, there is thickening of the nail plate which further hinders topical drug delivery.

Various topical therapies have been suggested for treatment of nail disorders, such as onychomycosis. Nail lacquers, coating, polishes, enamels, and varnishes have been described. Bohn, U.S. Pat. No. 4,957,730, describes a nail varnish containing a water-insoluble film-forming substance and antimycotic compound. Ferro, U.S. Pat. No. 5,120,530, describes an antimycotic nail varnish containing amorolfine in quaternary ammonium acrylic copolymer. The water-insoluble film former is a copolymerizate of acrylic acid esters and methacrylic acid esters having a low content of quaternary ammonium groups. Bohn, U.S. Pat. No. 5,264,206, describes a nail lacquer with antimycotic activity, which contains an antimycotic agent and water-insoluble film formers including polyvinyl acetate, a copolymer of polyvinyl acetate and acrylic acid, copolymers of vinyl acetate and crotonic acid. Wohlrab, U.S. Pat. No. 5,346,692, describes a nail lacquer for treating onychomycosis, comprised of a film-forming agent, an antimycotically active substance, and urea, wherewith the antimycotic agent and urea are liberated from the lacquer when the lacquer is applied. A preferred formulation comprises cellulose derivatives as film former, clotrimazole as the antimycotic agent, dibutyl phthalate as a plasticizer, and a mixture of acetone and ethanol as solvent. Nimni, U.S. Pat. No. 5,487,776, describes a nail lacquer composition which forms a water permeable film containing griseofulvin when the organic solvent system evaporates, wherein a portion of the griseofulvin is in solution and a portion of griseofulvin is present as a colloidal suspension. Chaudhuri, U.S. Pat. No. 6,143,794, describes a topical formulation for the treatment of nail fungal infections that includes an antifungal, solvent, gelling agent, adhesion-promoting agent, film-forming agent, surfactant, and optionally a keratolytic agent. The adhesion-promoting agent was a hydroxy-terminated polyurethane such as polyolprepolymer-2. All of these patents and publications describe products applied to the nail that form a substantive nail coating or film containing a drug from which the drug is to penetrate into the nail. None of these methods has proven to be consistently effective in treating disorders of the nail such as onychomycosis.

Various topical therapies utilizing chemical compounds disclosed to enhance penetration through the nail have been described. Knowles, U.S. Pat. No. 5,652,256, describes the use of methyl acetate as a penetration enhancing compound in combination with naftifine or sulconazole and naftifine as a topical gel for fungal treatment of the nails. Sorenson, U.S. Pat. No. 5,972,317, discloses that a proteolytic enzyme such as papain, delivered by pads soaked in the enzyme solution, produces a more permeable nail. Sun, U.S. Pat. No. 6,231,875, describes acidified compositions of antifungals to enhance transport across nails and skin. Reeves, U.S. Pat. No. 6,391,879, describes the combination of an anti-fungal agent dissolved in an anhydrous blend of polyglycol and DMSO. Although these and other enhanced penetration formulations were reported to increase penetration through the nail, they have not been shown to be clinically effective in treating conditions of the nail, such as onychomycosis.

Birnbaum, U.S. Pat. No. 7,135,194 discloses a solution to the problem of topical delivery of medications through the nail plate in a nail afflicted with onychomycosis. Onycholysis and the formation of an air gap between the nail plate and nail bed is common in onychomycosis. The air gap presents a major barrier to delivering drug to the nailbed.

Birnbaum solves this problem by incorporating an antifungal drug into a solid or semisolid composition, forcing the composition into the subungual space in the gap between the hyponychium and the nail bed, and packing this space with the solid or semisolid composition.

Presently, the only topical antifungal product approved by the FDA for treating onychomycosis is Ciclopirox Nail Lacquer 8% e.g. Penlac® manufactured by Sanofi Aventis, Bridgewater, N.J. The prescribing information for Penlac® reports the clinical effectiveness in two placebo-controlled studies in onychomycosis patients with target great toenail involvement of 20 to 65%. Patients applied Penlac® nail lacquer once daily for 48 weeks and were evaluated for effectiveness at the end of treatment (i.e. 48 weeks or last observation). Complete cure was defined as clear nail and negative mycology (absence of the causative fungus by culture and microscopic tests). Almost clear was defined as 10% or less nail involvement and negative mycology.

TABLE 1

|  |  | Study 312 | | Study 313 | |
| --- | --- | --- | --- | --- | --- |
|  |  | Penlac ® | Vehicle | Penlac ® | Vehicle |
| Complete Cure | # | 6/110 | 1/109 | 10/118 | 0/117 |
|  | % | 5.5 | 0.9 | 8.5 | 0 |
| Almost Clear | # | 7/107 | 1/108 | 14/116 | 1/115 |
|  | % | 6.5 | 0.9 | 12 | 0.9 |

As shown in Table 1, treatment with Penlac provided a low level of efficacy. Only 5.5% of treated patients were completely cured and only 6.5% of patients were almost cleared of onychomycosis. However, despite the low effectiveness of topical Ciclopirox Nail Lacquer in treating onychomycosis, the FDA approved Penlac because of the unmet medical need for a safe treatment for onychomycosis and the improved safety of topical applications over systemic anti-fungal agents.

Because of the difficulty in obtaining clinically effective concentrations of medication to the nail bed by topical application of a pharmaceutical composition to the affected nail, nail disorders, such as onychomycosis, are typically treated with systemic medications or with topical medications following removal of the nail. Systemic treatment for onychomycosis and other nail disorders is often not satisfactory because therapy must be continued for long periods of time, often many weeks or months, and the medication has effects on tissues other than on the affected nail. Antifungal compounds, such as miconazole and ketoconazole, have been demonstrated to be effective in topically treating onychomycosis after nail removal. However, it is clear that removal of the nail is a measure than most individuals suffering from onychomycosis would prefer not to undergo if a less drastic therapeutic method would be efficacious.

A select few oral antifungals such as Terbinafine hydrochloride tablets (Lamasil®, Novartis Pharmaceuticals Corporation, East Hanover, N.J.) are approved in the USA to treat onychomycosis. According to the prescribing information for Lamasil® tablets, only 38% of patients achieved a complete cure, defined as mycological cure plus no nail involvement for toenail onychomycosis in a 48 week study of Lamasil® treatment for 12 weeks and an efficacy evaluation made after a 36 week follow-up period in order to allow time for involved nail to grow out. Besides the low level of efficacy for Lamasil®, a variety of adverse reactions were reported for Lamasil® in the clinical studies including diarrhea, dyspepsia, abdominal pain, liver test abnormalities, rashes, urticaria and pruritis. The proscribing information for Lamasil® warns of rare cases of liver failure, some leading to death or liver transplant, and isolated reports of serious skin reactions. Additionally, Lamasil® tablets are not recommended for pregnant women or nursing mothers.

Another oral antifungal drug approved to treat onychomycosis of the toenails is itraconazole, available as 100 mg capsules under the Sporanox® brand from PriCare, divisions of Ortho-McNeil-Janssen Pharmaceuticals, Inc., Raritan, N.J. The prescribing information for Sporanox® capsules reports 14% complete cures (mycological cures plus clear nails) in 214 patients, who were given 200 mg of itraconazole daily for 12 consecutive weeks. Numerous adverse effects were reported including nausea, vomiting, diarrhea, abdominal pain, edema, fever, fatigue, rash, pruritus, headache, dizziness, hypertension, hypokalemia and abnormal hepatic function. The prescribing information warns that Sporanox® has been associated with rare cases of serious hepatotoxicity, including liver failure and death. A further warning to prescribers is that Sporanox® should not be administered for the treatment of onychomycosis in patients with evidence of ventricular dysfunction such as congestive heart failure.

Pitre, U.S. Patent Publication 2007/0041910, filed as U.S. patent application Ser. No. 11/432,410; and Mallard, U.S. Patent Publication 2006/0147383, filed as U.S. patent application Ser. No. 11/315,259, disclose that application of a pharmaceutical composition containing a vehicle, a volatile silicone, and a non-volatile oily phase, provides increased penetration of a pharmaceutically active compound when topically applied to skin or mucous membrane. This enhanced penetration is obtained without the use of glycols, such as propylene glycol, which are known to augment skin penetration of pharmaceutical compounds but which are also known to be irritating to skin. The formulations of Pitre and Mallard contain at least 25% w/w of a volatile silicone and, if formulated with an alcoholic vehicle, contain at least 15% of alcohol. All alcoholic compositions disclosed in Pitre and Mallard contain greater than 50% volatile silicone and the concentration of the volatile silicone is at least twice the concentration of the alcohol in the composition.

Pitre and Mallard do not disclose or suggest the use of such compositions for the treatment of diseases of a nail, such as onychomycosis. Moreover, studies have been conducted, including studies conducted in the laboratories of the present inventors, which show that the penetrating ability of an active agent from a composition into skin cannot be correlated to the penetrating ability of the active agent from the composition into or through a nail.

A significant need remains for a pharmaceutical composition that provides for enhanced penetration of a pharmaceutical agent contained within the composition into and through a nail and into the nail bed. Such a composition would be valuable for topically treating conditions affecting the nail or nail bed, such as onychomycosis.

DESCRIPTION OF THE INVENTION

Figure 1:
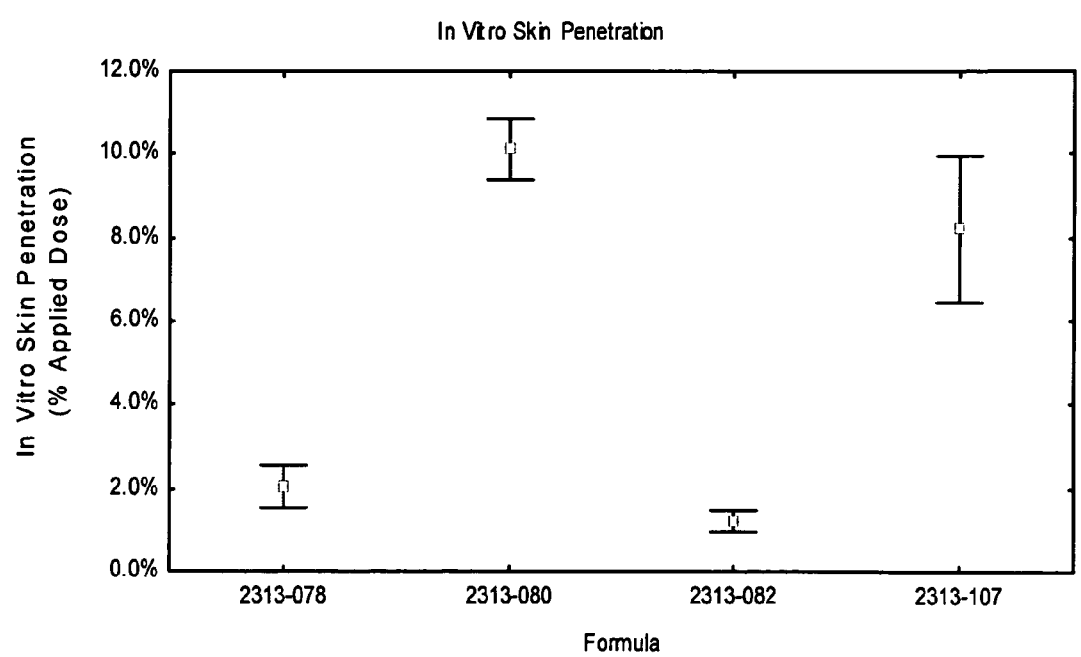
FIG. 1 is a graph showing the in vitro penetration of KP-103 through skin from a formulation of the invention and from three prior art formulations.

It has been unexpectedly discovered that a pharmaceutical composition containing an active pharmaceutical ingredient (API), a solvent, referred to herein as the "vehicle" or the "volatile vehicle", a wetting agent which may or may not be the same compound as the vehicle, and a non-volatile solvent which has limited water miscibility, having a surface tension of 40 dynes/cm or less, and which composition does not form a solid film when applied to the surface of a nail, provides enhanced penetration of the API through an intact nail and into the nailbed. Preferably, the composition of the invention is free of film forming polymeric compounds. It is conceived that such compositions may be used to deliver an API in order to treat medical conditions involving the nail and/or the underlying nail bed.

It has been further unexpectedly discovered that one of the mechanisms by which the pharmaceutical composition described herein is effective in treating medical conditions involving the nail or nail bed is due in part to the low surface tension of the composition. Because the composition of the invention has a low surface tension, that is 40 dynes/cm or less, when the composition is applied to the surface of the nail, and because the composition when applied to the nail does not form a solid film, not only does the active ingredient penetrate the nail to reach the nail bed, but the composition spreads to wet the nail folds and is also wicked by capillary action into the gap between the nail and nail bed, without the need to provide pressure or to otherwise force the composition into the gap.

Additionally, the preferred lack of film forming polymeric compounds in the composition contributes to the wickability of the composition into the gap between the nail and the nail bed as well as the nail folds.

In one embodiment, the invention is a pharmaceutical composition for the treatment of disorders of the nail or nail bed. The pharmaceutical composition of the invention contains a volatile and/or penetrating vehicle, a non-volatile solvent that is dissolved, suspended, dispersed, or emulsified within the vehicle, an API that is soluble in the non-volatile solvent and/or a mixture of the vehicle and the non-volatile solvent and is optionally soluble in the vehicle, and a wetting agent, which may or may not be the vehicle itself. The surface tension of the pharmaceutical composition is preferably 40 dynes/cm or less. In a preferred embodiment, the surface tension of the pharmaceutical composition is 35 dynes/cm or less, more preferably 30 dynes/cm or less, and most preferably 25 dynes/cm or less. Preferably, the composition is free of polymeric film forming compounds.

In another embodiment, the invention is a pharmaceutical formulation for delivery of an API to the nail or nail bed in order to treat disorders of this area. According to this embodiment, the formulation contains a volatile and/or penetrating vehicle, a non-volatile solvent that is dissolved, suspended, dispersed, or emulsified within the vehicle, and a wetting agent, which may or may not be the vehicle. The surface tension of the pharmaceutical formulation is 40 dynes/cm or less, preferably 35 dynes/cm or less, more preferably 30 dynes/cm or less, and most preferably 25 dynes/cm or less. Preferably, the formulation is free of polymeric film forming compounds. The API that is to be used with the formulation of the invention is one that is soluble in the non-volatile solvent and/or a mixture of the vehicle and the non-volatile solvent and is optionally soluble in the vehicle alone.

In another embodiment, the invention is a method for treating a disorder of the nail or nail bed. According to this embodiment of the invention, a pharmaceutical composition containing a volatile and/or penetrating vehicle, a non-volatile solvent that is dissolved, suspended, dispersed, or emulsified within the vehicle, an API that is soluble in the non-volatile solvent and/or a mixture of the vehicle and the non-volatile solvent and is optionally soluble in the vehicle alone, and a wetting agent, which may or may not be the vehicle itself, is topically applied to the surface of a nail that is suffering from a disorder in an amount and for a time sufficient to ameliorate the symptoms of the disorder. The surface tension of the pharmaceutical composition is 40 dynes/cm or less, preferably 35 dynes//cm or less, more preferably 30 dynes/cm or less, and most preferably 25 dynes/cm or less. Preferably, the composition is free of polymeric film forming compounds.

As used herein, the term "volatile" when referring to the vehicle means that the vehicle is a compound that evaporates from the surface of the nail when applied. Volatile vehicles are compounds which have a measurable vapor pressure, and preferably are compounds that have a vapor pressure of greater than about 100 Pa at room temperature. Examples of volatile vehicles include: acetone, 2-amino-2-methyl-1-propanol, 1,2-butanediol, 1,4-butanediol, 2-butanol, cyclomethicone-4, cyclomethicone-5, cyclomethicone-6, ethanol, ethyl acetate, n-heptane, isobutanol, isopropyl alcohol, 1-propanol, 2-propanol, and water.

As used herein, the term "penetrating" when referring to the vehicle means that the vehicle is a compound that rapidly penetrates into a nail when applied to the surface of the nail so that, after 10 minutes following the application of a thin layer of the vehicle onto the surface of a nail, no more than 10% of the applied amount remains on the nail surface. The term penetrating@ thus includes both volatile and non-volatile vehicles.

As used herein, the term "surface tension" refers to the force required to increase unit area of a surface of a liquid or of an interface between two liquids or between a liquid and a gas, generally stated in units of dynes/cm. Surface tensions described herein are measured by the Du Noüy ring method utilizing an EasyDyne tensiometer model K20 marketed by Krüss USA, Matthews, N.C.

Examples of pharmaceutical compositions that may be used in the method of the present invention, provided such compositions have a surface tension of 40 dynes/cm or less, are disclosed in Pitre, U.S. patent application Ser. No. 11/432,410; and in Mallard, U.S. patent application Ser. No. 11/315,259, which applications are incorporated herein in their entirety. In accordance with the present invention, the pharmaceutical compositions of Pitre and Mallard that may be used to treat medical conditions of the nail in accordance with the present invention may contain Vitamin D as the API as disclosed in Pitre or clobetasol as disclosed in Mallard, or may contain other APIs in place of, or in addition to, these APIs, as disclosed herein.

The API of the composition of the invention is one that is useful in the treatment of a disorder of the nail or nail bed. The API is soluble in the solvent of the composition and/or in the combination of the solvent and vehicle of the composition. Examples of suitable APIs include anti-inflammatory agents, antimicrobial agents such as antibiotics and antifungal agents, anesthetic agents, steroidal agents, vitamins and derivatives thereof, anti-psoriatic drugs, and analgesic agents.

In a preferred embodiment, the API of the composition of the invention is an antifungal chemical compound, particularly those effective in the treatment of onychomycosis. Examples of suitable antifungal agents include polyene antimycotic agents such as natamycin, rimocidin, filipin, nystatin, and amphotericin B; imidazole compounds such as miconazole, ketoconazole, clotrimazole, econazole, bifonazole, butoconazole, fenticonazole, isoconazole, oxiconazole, sertaconazole, suconazole, and tioconazole; triazole compounds such as fluconazole, itraconazole, ravuconazole, posaconazole, voriconazole, (2R,3R)-2-(2,4-difluorophenyl)-3-(4-methylenepiperidine-1-yl)-1-(1H-1,2,4-triazole-1-yl)butane-2-ol (referred to herein as "KP-103"), and terconazole; allylamine compounds such as terbinafine, amorolfine, naftifine, and butenafine; echinocandin compounds such as anidulafungin, caspfungin, and micafungin; and other antifungal drugs such as ciclopirox, flucytosine, griseofulvin, gentian violet, haloprogin, tolnaftate, and undecylenic acid. Any antifungal compound suitable for pharmaceutical use in humans or mammals, and particularly those which are active in vitro against *Candida albicans, Trichophyton rubrum* or *Trichophyton mentagrophytes*, is suitable for the API of the invention. Particularly preferred are antifungal APIs that have relatively low binding to keratin, such as triazole compounds like KP-103.

Other APIs that are suitable for the composition of the invention include those that are effective in treating diseases and disorders of nails other than onychomycosis, especially those diseases and disorders affecting tissues deep to the external surface of the nail, such as the internal portion of the nail, the deep nail surface adjacent to the nail bed, and the nail bed. Such diseases and disorders may include onychia, onychocryptosis, onychodystrophy, onychogryposis, onycholysis, onychomadesis, onychophosis, onychoptosis, paronychia, koilonychia, subungual hematoma, and laminitis. Drugs other than antifungal agents that are suitable for the composition of the invention include corticosteroids such as clobetasol propionate, betamethasone dipropionate, halobetasol propionate, fluocinonide and mometasone furoate, keratolytic agents such as urea and salicylic acid, or antibacterials/antibiotics such benzoyl peroxide, mupirocin, erythromycin, bacitracin, chlorotetracyciline and cetylpyridinium chloride.

The vehicle of the composition of the invention is a pharmaceutically acceptable vehicle in which the constituents of the composition of the invention can be dissolved, suspended, disbursed, or emulsified. The constituents of the composition may be all within a single phase in the vehicle. For example, the API, wetting agent, and the non-volatile phase may be dissolved in the vehicle. Alternatively, the constituents may occupy separate phases within the vehicle. For example, the API may be dissolved in the vehicle and the other constituents may be suspended, dispersed, or emulsified in solvent. For another example, the API may be dissolved in the solvent which is suspended, dispersed, or emulsified in the vehicles, with the remaining constituents being dissolved in either the vehicle or the solvent. Preferably, but not necessarily, the API, wetting agent, and non-volatile phase are all miscible in the vehicle.

Examples of suitable vehicles include one or more of water, alcohols, polyols, ethers, esters, aldehydes, ketones, fatty acids, fatty alcohols, and fatty esters. Specific examples of suitable vehicles include ethanol; 3-propanediol; 1,2-butanediol; 1,2,3-propanetriol; 1,3-butanediol; 1,4-butanediol; isopropyl alcohol; and 2-amino-2-methyl-1-propanol. In a preferred embodiment, the vehicle is an alcohol, and most preferably a linear or branched aliphatic lower alcohol, such as methanol, ethanol, propanol, or isopropanol.

The wetting agent of the composition of the invention is a chemical compound that reduces the surface tension of liquid compositions and does not build viscosity. Any surfactant or group of surfactants that is suitable for dermatologic applications is suitable for the invention. Such surfactants may function as wetting agents in the compositions of the invention, and as emulsifiers or solubilizers. The surfactants may be nonionic, anionic, cationic, zwitterionic, amphoteric, or ampholytic surfactants.

Examples of non-ionic surfactants include polyoxyethylene sorbitan fatty acid esters such as polysorbate 20, 40, 60 and 80; sorbitan esters such as sorbitan monolaurate, sorbitan monooleate, sorbitan monostearate, and sorbitan trioleate; polyoxyethylene alkyl ethers such as Brij 30, Brij 97, Emulgen 104P, 210P, 200 and Ethylan 253, 254, 256, and 257, polyoxyethylene castor oil derivatives such as polyoxyl 35 castor oil.

Examples of cationic surfactants include fatty amines; quaternary ammonium compounds; as well as cationic copolymers, cationic mixed polymers, cationic polysaccharides, cationic cellulose derivatives, cationic or cationized hydrolyzed proteins such as collagen or keratin, or a mixture thereof. Specific examples of cationic surfactants include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallow trimethylammonium chloride, cocotrimethylammonium chloride, and the corresponding hydroxides thereof; quaternary esters, such as tetradecylbetaine ester chloride; diquaternary esters, such as dipalmitoylethyldimethylammonium chloride; and diquaternary silicones.

Examples of anionic surfactants include but are not limited to those based on sulfate, sulfonate, or carboxylate anions. Examples of such anionic surfactants include sodium laureth sulfate, alkyl benzene sulfonates, soaps, fatty acid salts, and alkyl sulfate salts such as sodium lauryl sulfate, also known as sodium dodecyl sulfate, and ammonium lauryl sulfate.

Examples of amphoteric (zwitterionic) surfactants include but are not limited to dodecyl betaine, dodecyl dimethylamine oxide, cocamidopropyl betaine, and cocoamphoglycinate.

Preferably, the wetting agent is a volatile silicone. Such volatile silicones include linear or cyclic polyorganosiloxane compounds of formula $[R_1SiOR_2]_n$ wherein n=6 or less and $R_1$ and $R_2$ are alkyl groups that may be the same or different, and which compound has a measurable vapor pressure under ambient conditions. Preferably, n=from 3 to 6, and most preferably n=4 or 5. Preferably $R_1$ and $R_2$=methyl.

Examples of cyclic volatile silicones include polydimethylcyclosiloxanes, generally known as cyclomethicones. Particular examples of cyclic volatile silicones include cyclopentasiloxane, cyclotetrasiloxane, decylmethylcyclopentasiloxane, and octylmethylcyclotetrasiloxane. Examples of linear volatile silicones include linear polysiloxanes. Particular examples of linear volatile silicones include hexamethyldisiloxane, octamethyltrisiloxane, and dimethicones.

In one particular embodiment of the invention, a single compound forms both the vehicle and the wetting agent of the composition. For example, the vehicle may be a volatile silicone. In this situation, the volatile silicone may also be the wetting agent of the composition. In the case in which the wetting agent serves also as the vehicle, the concentration of the wetting agent in the composition is sufficiently high to function as a vehicle in which all other components of the composition are dissolved, suspended, dispersed, or emulsified.

The non-volatile solvent of the composition is a non-aqueous solvent that may or may not be soluble or miscible in the vehicle of the composition. The API of the composition is preferably, but not necessarily, soluble in the non-volatile solvent. In a preferred embodiment wherein the API is hydrophilic, the non-volatile solvent is a polar or semi-polar molecule. In another preferred embodiment wherein the API is hydrophobic, the non-volatile solvent is non-polar.

Suitable non-volatile solvents for hydrophobic drugs are disclosed in Pitre, U.S. patent application Ser. No. 11/432, 410 in paragraphs 0069 to 0082, which paragraphs are incorporated herein by reference. For example, the non-volatile solvent may be an ester of the formula RCO—OR', wherein R and R' may be identical or different and each of R and R' represents a linear or branched chain of an alkyl, alkenyl, alkoxycarbonylalkyl, or alkoxycarbonyloxyalkyl radical having from 1 to 25 carbon atoms, preferably from 4 to 20 carbon atoms. The non-volatile solvent may be a glyceryl ester of a fatty acid, such as fatty esters of natural fatty acids or triglycerides of animal or plant origin. The non-volatile solvent may be a fatty acid glyceride, including synthetic or semi-synthetic glyceryl esters, such as fatty acid mono-, di-, or triglycerides, which are oils or fats. The non-volatile solvent may be a non-volatile hydrocarbon, such as paraffins, isoparaffins, and mineral oil. The non-volatile solvent may be a guerbet ester. The non-volatile solvent may be a non-volatile silicone, provided that the presence of the non-volatile silicone in the composition does not result in the formation of a hard polymeric film upon application of the composition onto a nail. Included within such non-film forming silicones are polyorganosiloxane compounds that have the formula $[R_1SiOR_2]_n$, wherein n>6 and $R_1$ and $R_2$ are alkyl groups that may be the same or different, and which compound may or may not have a measurable vapor pressure under ambient conditions.

Other examples of suitable non-volatile solvents for hydrophobic drugs in addition to those disclosed in Pitre include squalane, dibutyl sebacate, isopropyl laurate, isopropyl myristate, isopropyl palmitate, isopropyl strearate, myristyl alcohol, oleyl alcohol, oleic acid, lauryl lactate, myristyl lactate, mixed C12-15 alkyl lactates, diisopropyl adipate, octyldodecanol, caproic acid, caprylic acid, capric acid, lauryl benzoate, myristyl benzoate, mixed C12 15 alkyl benzoates, benzyl benzoate, tridecyl neopentanoate, light mineral oil, mineral oil, and alpha terpineol. Examples of suitable non-volatile solvents for hydrophilic drugs include diethylene glycol monoethyl ether, n-methylpyrrolidone, dimethyl sulfoxide, ethyl lactate, hexylene glycol, glycerol, benzyl alcohol and glycerol triacetate.

The composition of the invention may contain additional optional components, such as preservatives, stabilizers, lubricants, humectants, moisture regulators, foaming agents, binders, pH regulators, osmotic pressure modifiers, emulsifiers, antioxidants, colors, aerosol propellants, fragrances, or odor maskers. If desired, the composition may also contain additional nail modifiers or penetration enhancers, such as urea, propylene glycol, sodium lauryl sulfate, and glycolic acid.

The composition is intended to remain in a liquid or semi-solid state after application to the nail and does not form a hard lacquer, shell, or film on the nail following application, which occurs by a process of solvent casting following evaporation of a volatile solvent which leaves behind a solid residue that forms the lacquer, shell or film which is lasting, hard, and/or adherent. Therefore, it is preferred that the components of the composition are miscible in the composition and also are miscible in the "secondary" composition that remains after the volatile vehicle has evaporated or penetrated the nail. It is also suitable for the components of the composition, other than the vehicle, to be suspendible, dispersible, or emulsifiable, in the secondary composition, such as in the non-volatile solvent.

The composition has a surface tension that is sufficiently low so that, when the composition is applied to the surface of a toenail on a human subject, the composition spreads into the nail folds and also is wicked into the gap between the nail and the nail bed if such a gap is present. A gap is generally present in a nail that is suffering from a disorder such as onychomycosis. Preferably, the surface tension of the composition is 40 dynes/cm or less, more preferably 35 dynes/cm or less, even more preferably 30 dynes/cm or less, and most preferably, the surface tension is 25 dynes/cm or less.

It is preferred that the composition, when applied to the surface of a nail, does not form a solid film or lacquer and it is most preferred that the composition is free of polymeric film forming compounds. Examples of polymeric film forming compounds include polymers and copolymers of polyvinyl acetate, polyvinylpyrrolidone, methacrylic acid, polyvinyl butyrals, polyvinyl acetals, and cellulose derivatives such as cellulose acetate phthalate, cellulose acetate butyrate, cellulose acetate propionate, cellulose nitrate, cellulose sulfate, ethylcellulose, and cellulose acetate. A polymeric film forming agent may be present in the composition of this application if it is present in an amount below that which will result in the formation of a film or lacquer following application of the composition to the surface of a nail.

The spreadability of a composition may be defined by a test such as the single slide spreadability test, which may be performed as follows. One hundred microliters of a test formulation is applied to a single point on the surface of a clean dry single glass slide. The area of spread of the formulation on the glass slide is determined at various times following the application, such as at 1, 2, 4, 6, and 10 minutes. Formulations that are most suitable for the present method continue to spread on the surface of the slide throughout the first 6 minutes and preferably throughout the first 10 minutes. Preferably, but not necessarily, the area of coverage of the formulation on the slide after 10 minutes is higher than 11.0 cm$^2$.

The composition of the invention may be prepared in any number of forms, such as creams, milks, salves, impregnated pads, solutions, tinctures, liniments, liquids, sprays, foams, suspensions, gels, or lotions. The composition may be formulated to provide for immediate or controlled release of the API from the composition.

The concentration of the various essential and optional components of the composition of the invention will vary, depending on the particular components contained in the composition, the form of the composition, the particular disease or condition that is to be treated with the composition, and whether the formulation is for immediate or for controlled release.

The API of the composition is at a concentration that is effective to treat a disorder or disease of the nail or nail bed. Typically, the concentration of the API will constitute between 0.0001 to 30% or higher by weight of the composition.

The concentration of the wetting agent in the composition may vary depending on several factors, including the identity of the wetting agent and whether the wetting agent is also the vehicle of the composition. Generally, the concentration of the wetting agent, such as a volatile silicone, will be between 0.001% and 95% by weight of the composition. Preferably, the concentration of the wetting agent is between 0.01% and 80%, more preferably between 0.1% and 60%, and most preferably between 1% and 40% w/w of the composition. In a particularly preferred embodiment, the concentration of wetting agent in the composition is between 2% and 15% w/w. In the case where the wetting agent is not functioning as a vehicle of the composition, the concentration of wetting agent in the composition will generally be towards the lower end of the above range of concentration, such as between 0.001% and 10%.

The concentration of the non-volatile solvent will constitute between 0% and 90% w/w of the composition. Generally, with less viscous forms of the compositions, lower concentrations of non-volatile phase will be present, and with more viscous forms, higher concentrations of the non-volatile phase will be used. Also, predominately oil-based compositions tend to have a higher concentration of non-volatile phase or components than do compositions such as sprays, gels, and lotions and so will have a higher concentration of a non-volatile solvent. Typical concentrations of non-volatile solvent are between 10 and 80%, with preferred concentrations being between 12 and 60%, and most preferred concentrations between 15 and 50% w/w.

The concentration of the vehicle will be that which is sufficient to dissolve, suspend, disperse, or emulsify the other components of the composition. In many but not all cases, the concentration of the vehicle will be higher than that of any other constituent of the composition. In some cases, the concentration of the vehicle will be higher than that of the combined concentration of the other constituents of the composition. In a preferred embodiment in which the vehicle is an alcohol, the composition will contain at least 10% alcohol, more typically at least 15% alcohol, and most typically at least 25% alcohol. The concentration of alcohol in the composition may be as high as 80%, or higher. In one preferred embodiment, the concentration of alcohol is at least 50% w/w of the composition.

In a particularly preferred embodiment of the invention, the composition of the invention is an alcoholic composition containing a volatile silicone. In a first preferred embodiment, the ratio of alcohol to volatile silicone in the composition % w/w is at least 2:3, preferably at least 1:1, more preferably at least 2:1, and most preferably at least 3:1. In a second preferred embodiment, the concentration of the volatile silicone in the composition is less than 25% w/w. In a third preferred embodiment, the concentration of the alcohol in the composition is at least 40%, more preferably at least 45%, and most preferably at least 50% w/w. The composition of the invention, according to this embodiment of the invention, may be made so as to encompass any one, two, or all three of the embodiments described above. It has been determined that, when applied to the surface of a nail, the alcoholic composition of the invention containing a volatile silicone provides a high degree of penetration of an API contained therein into the nail.

Although the compositions of the invention may be used to treat various diseases and disorders of the skin or mucous membranes, they are most advantageously used to treat conditions involving the nails of the hands or feet. The compositions and methods of the invention provide increased penetration of API in the composition into and through the nail and to the nail bed. The compositions of the invention may be used effectively to treat diseases and disorders in humans or in other animals, such as cats, dogs, horses, cattle, sheep, goats, pigs, and birds. In human and in veterinary patients, the compositions of the invention may be used, depending on the particular animal treated, to treat conditions involving nails, hooves, horns, or beaks.

The compositions of the invention are especially well suited for the treatment of onychomycosis and other disorders of the nail and nail bed. The composition is topically applied to the surface of the nail and surrounding tissue by any means by which the composition may be applied. The method of application may vary depending on the physical state of the composition, whether it is in a liquid, semisolid, or solid form, and on the viscosity of the composition if it is a liquid. Thus, for example, the composition may be rubbed, painted, dabbed, dripped, sprayed, wiped, spread, or poured onto the affected nail and surrounding tissues, or utilized as a soak. Frequency of treatment and duration of therapy will very depending on several factors, including the condition that is being treated, the identity and concentration of the API in the composition, and constituents of the composition other than the API. Typically, the frequency of treatment will be twice daily to once weekly, and preferably once daily. The preferred duration of topical treatment is at least 36 weeks and preferably longer, such as 40 weeks or 48 weeks. The preferred criterion for treatment efficacy is complete cure, which can be assessed at the end of treatment, but is preferably assessed 4 to 12 weeks after the end of treatment, most preferably 4 weeks after the end of treatment.

To further illustrate the invention, the following examples are provided. It is to be understood that these examples are provided for illustrative purposes and are not to be construed as limiting the scope of the invention. It is to be further understood that, in the examples the functions of individual ingredients are sometimes listed for illustration purposes. However, it is understood that not all functions of the ingredients are listed and that many excipients have multiple functions.

Example 1

Skin Penetration Study

Four different formulations were tested to determine the penetrability of an API into skin. The formulations each contained 5.00% w/w of a triazole antifungal API compound, KP-103. The compositions of the four formulations are shown in Table 2. All concentrations of the components of the formulations are in % w/w.

TABLE 2

| | Formulation No. | | | |
|---|---|---|---|---|
| | 078 | 080 | 082 | 107 |
| KP-103 | 5.00 | 5.00 | 5.00 | 5.00 |
| alcohol | 19.35 | 20.00 | 59.998 | — |
| triacetin | 15.00 | — | — | — |
| glycerin | 35.00 | 24.998 | — | — |
| 1,3-butylene glycol | 25.00 | — | — | — |
| carbomer 980 | 0.50 | — | — | — |
| diisopropanolamine | 0.10 | — | — | — |
| Vitamin E | 0.05 | 0.002 | 0.002 | 0.05 |
| propylene glycol | — | 50.00 | — | — |
| cyclomethicone | — | — | 13.00 | — |
| diisopropyl adipate | — | — | 12.00 | 8.20 |
| myristyl lactate | — | — | 10.00 | — |
| isopropyl myristate | — | — | — | 5.48 |
| white petrolatum | — | — | — | 51.27 |
| urea | — | — | — | 30.00 |

Each of the formulations of Table 2 was spiked with tracer amounts of radiolabeled KP-103 at approximately 0.90 μCi/dose. A single clinically relevant dose (5 mg/cm2) was applied to dermatomed human skin obtained from one donor following elective surgery.

Percutaneous absorption was evaluated by mounting the dermatomed tissue in Bronaugh flow-through diffusion cells at 3° C. Six replicates were performed for each formulation. Fresh receptor fluid, PBS containing 0.1% w/v sodium azide and 1.5% Oleth-20, was continuously pumped under the skin at a nominal flow rate of 1 ml/hr and collected in 6-hour intervals. Following 24-hours of exposure, the residual formulation remaining on the skin surface was removed by repeated tape stripping (5 strips/cell). Subsequently, the epidermis was physically separated from the dermis by gentle peeling. The quantity of radioactivity in the tape-strips, epidermis, dermis, and receptor fluid samples was determined using liquid scintillation counting. The results for the calculated quantity of API collected in the receptor for each of the formulations of Table 2 are shown in FIG. 1.

As shown in FIG. 1, Formulations 080 and 107 demonstrated considerably higher skin penetration than did Formulations 078 and 082. Formulation 080 contains propylene glycol, a known skin-penetration enhancer, and exhibited a higher penetration through skin than any of the other formulations. Formulation 107 contains urea, a known skin-penetration enhancer, and exhibited the second highest skin penetration of the four formulations tested. Formulation 082 is a formulation according to the present invention and exhibited the lowest skin penetration of the tested formulations. Formulation 078 is a composition that is not within the scope of the invention and exhibited slightly higher penetration into and through skin than did Formulation 082. Of the four formulations, the formulation with the lowest level of skin penetration was formulation 082, the only formulation of the four that is a composition of the invention.

Example 2

Nail Penetration Study

The formulations 078, 080, 082, and 107 of Example 1 were tested to determine penetration of the API from the formulation into and through nail plates. Each of the formulations of Table 2 was spiked with tracer amounts of radiolabeled KP-103 at approximately 0.90 µCi/dose. A clinically relevant protocol was followed, which entailed dosing 10 µL/cm$^2$ per day for 14 days onto healthy human finger nail plates, which were obtained from multiple donors.

Nail penetration was evaluated by mounting the finger nail plates into custom diffusion cells. Five replicates were performed for each formulation. A small cotton ball wetted with 0.1 mL normal saline was used as a receptor. For each day of the study, the surface of the nail was washed, and 10 µL of formulation was applied to the surface. Every second day, the cotton ball receptor was replaced. After fourteen days of exposure, the nail plate was sectioned into three sections, a central dorsal (upper) section, central ventral (lower) section and the remaining peripheral material. The quantity of radioactivity in the daily surface washes, cotton ball receptors, dorsal nail, ventral nail and peripheral nail was determined using liquid scintillation counting.

Figure 2:
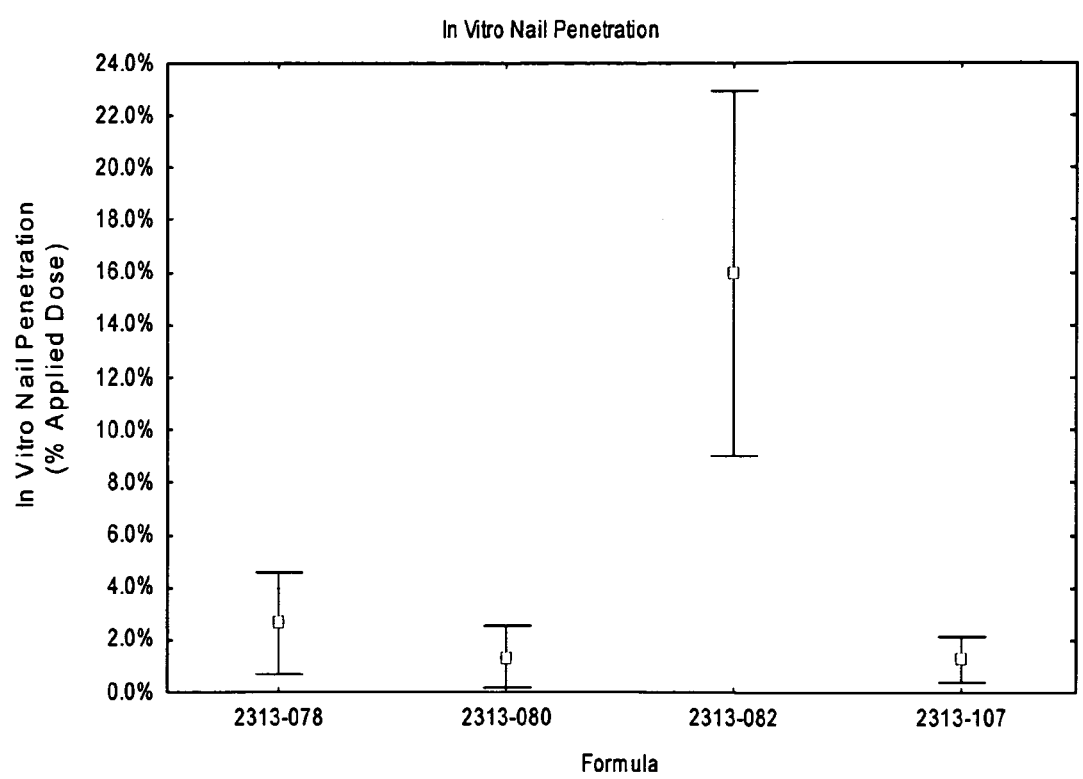
FIG. 2 is a graph showing the in vitro penetration of KP-103 through nail tissue from a formulation of the invention and from three prior art formulations.
Figure 3:
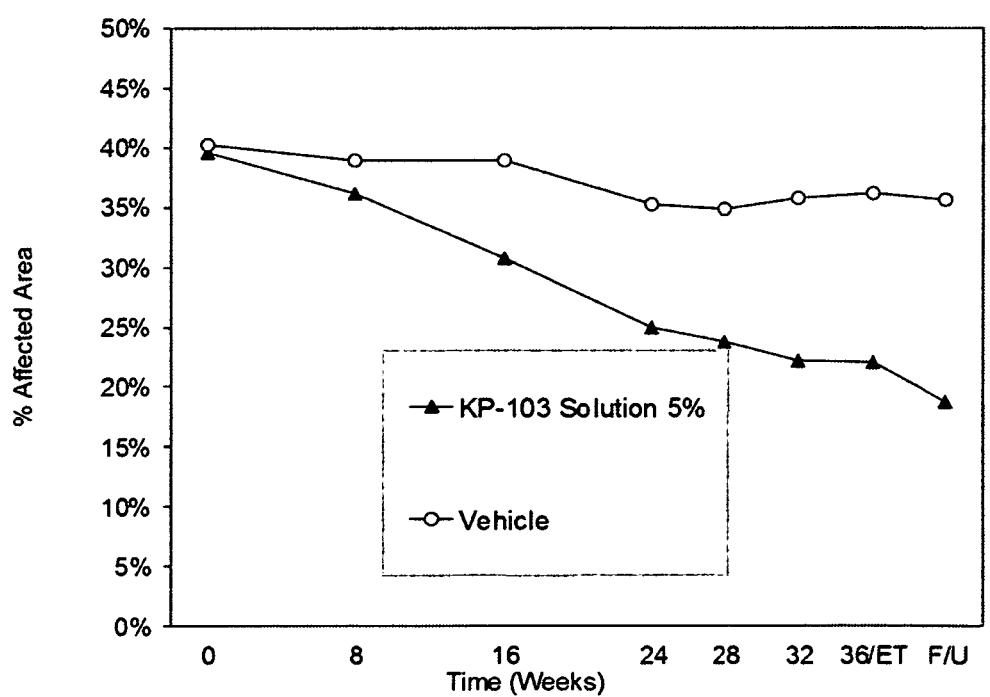
FIG. 3 is a graph showing the percentage of nail area affected by onychomycosis from pre-treatment through the follow-up assessment 4 weeks post treatment with a formulation of the invention compared to its vehicle.

The results are shown in FIG. 2. As shown in FIG. 2, the formulation of the invention, Formulation 082, provided over 6 times the penetration through the nail and into the saturated cotton ball receptor than did the other formulations, calculated as a percentage of the applied dose. The penetration of Formulations 080 and 107 had been expected to be highest through nail because they had exhibited a significantly higher penetration through skin. However, the penetration of API from Formulations 080 and 107 was, in fact, lower than from the other formulations even though these Formulations 080 and 107 contained well known skin penetration enhancers. This study establishes that the penetration of API from a formulation through skin is not predictive of the penetration of the API from the formulation through nail tissue. This study further establishes the unexpected ability of a preferred formulation of the invention, Formulation 082, to increase the penetration of API within the formulation through nail tissue.

Example 3

Clinical Assessment in Animal Model of Onychomycosis

The efficacy of a formulation of the invention, Formulation 087, containing 3.00% w/w of a triazole antifungal API, KP-103, was evaluated in an animal model of onychomycosis and, in two separate studies, was compared with that of several commercial products intended for the treatment of onychomycosis. The composition of Formulation 087 is shown in Table 3.

TABLE 3

FORMULATION 087

| Component | Concentration (% w/w) |
|---|---|
| KP-103 | 3.00 |
| Alcohol | 60.00 |
| Vitamin E | 0.002 |
| Cyclomethicone | 13.00 |
| Diisopropyl adipate | 10.00 |
| Myristyl lactate | 13.998 |

In order to test the efficacy of Formulation 087 and the comparison products, onychomycosis was induced in six-week old Hartley guinea pigs. Each of Formulation 087 and the comparison products were tested in five animals. Two hundred (200) µL of a suspension of *Trichophyton mentagrophytes* SM-110 (1×10$^8$ arthrospores/mL) was inoculated to the plantar and interdigital skin of the hind paws, and the entire feet were then covered with bandage. The bandage was removed 28 days after fungal inoculation. Test treatments were applied for a period of 30 days, starting on the 60th day after infection.

The infected nails were removed from the feet 7 days following the final treatment and were minced with scissors. The nails were placed in a glass homogenizer and PBS (phosphate buffer solution) containing 0.25% porcine pancreatic trypsin was added at a rate of 1 mL/50 mg of wet nail weight, and the nail was homogenized. The homogenate was allowed to stand at 37°_C. for 1 hour. One hundred microliters of the nail homogenate or its dilution was spread on a GPLP agar medium containing antibiotics and cultured at 30° C. for 7 days. After culturing, the fungal colonies that appeared on the medium were counted, and the number of colony forming units (CFU) of fungi in the nails was calculated. The nail sample was considered culture-negative when no fungal colony appeared on the plate.

In Study 1, the efficacy of Formulation 087, applied to the nails at 30 µL/foot once a day for 30 days, was compared with untreated control animals and with 5% Amorolfine lacquer (Loceryl®) applied to the nails at 30 µL/foot once a week for 30 days. In Study 2, 1% naftifine gel (Naftin®) and 8% ciclopirox lacquer (Penlac®), each applied to the nails at 30 µL/foot once a day for 30 days, were compared with untreated control animals. The results of Study 1 and Study 2 are shown in Table 4.

TABLE 4

| Treatment | Mean no. of CFU in nails/foot after treatment (Log 10) | No. of feet with culture-negative nails/total no. of feet (%) after treatment |
|---|---|---|
| Study 1 | | |
| Control (no treatment) | 29512 (4.47 +/− 0.37) | N/A |
| 5% Amorolfine lacquer (Loceryl[7]) | 2398 (3.38 +/− 0.87) | 0/10 (0%) |
| Formulation 087 | 63 (1.80 +/− 0.53) | 6/10 (60%) |
| Study 2 | | |
| Control (no treatment) | 10964 (4.04 +/− 0.69) | N/A |
| 1% Ciclopirox lacquer (Penlac[7]) | 214 (2.33 +/− 1.10) | 1/10 (10%) |
| 1% Naftifine gel (Naftin[7]) | 501 (2.70 +/− 1.45) | 1/10 (10%) |

The data of Table 4 establishes that the formulation of the invention was more efficacious in treating onychomycosis in an animal model of human disease than were several currently available therapies for onychomycosis. With Formulation 087 of the invention, 60% of the infected nails were culture-negative following treatment. With the compositions of the prior art, 10% or less of the infected nails were culture-negative following treatment.

Example 4

Clinical Assessment in Human Treatment

An adult male human suffering from onychomycosis of the left large toenail was treated daily by topical application of a 10% topical formulation of the invention containing KP-103. Additional components of the 10% topical formulation were alcohol, vitamin E, butylated hydroxytoluene, cyclomethicone, diisopropyl adipate, and C12-15 alkyl lactates. Nail involvement at the initiation of treatment was 80% with onycholysis (separation of the nail plate from the nail bed) and thickening of subungual area. Following six months of treatment, the diseased proximal portion of the nail had grown out beyond the distal end of the nail plate (hyponychium) and was subsequently clipped off. There was no active fungal involvement of the nail plate, signs of onycholysis or thickening of the subungual area, or nail involvement after 6 months of treatment.

Example 5

Additional Formulations of the Invention Containing KP-103

Several additional formulations of the invention were made containing identical components, but in varying concentrations (% w/w), as shown in Table 5.

TABLE 5

| MATERIAL | FUNCTION | Formulation A 10% SOLUTION | Formulation B 5% SOLUTION | Formulation C VEHICLE |
|---|---|---|---|---|
| Alcohol | vehicle | 56.73 | 59.85 | 63.04 |
| Cyclomethicone | wetting agent | 12.30 | 13.00 | 13.67 |
| Diisopropyl adipate | non-volatile solvent | 11.36 | 12.00 | 12.62 |
| C12-15 alkyl lactate | non-volatile solvent | 9.46 | 10.00 | 10.52 |
| KP-103 | API | 10.00 | 5.00 | 0.00 |
| Vitamin E | anti-oxidant | 0.05 | 0.05 | 0.05 |
| Butylated hydroxytoluene | | 0.10 | 0.10 | 0.10 |

Example 6

Determination of Surface Tension

The surface tension of Formulation 087 shown above in Table 3 in Example 3 and the surface tension of the Formulations A, B, and C of Example 5 were determined at ambient room temperature of 21° to 25° utilizing about 30 grams of each solution on a Krüss Surface Tensiometer, Model K20 Easy Dyne (Krüss USA, Matthews, N.C.). The surface tension value for each of the formulations is shown below in Table 6.

TABLE 6

| | Formulation | | | |
|---|---|---|---|---|
| | Formulation 087 | Formulation A | Formulation B | Formulation C |
| Surface Tension (dynes/cm) | 22.1 | 22.1 | 22.0 | 21.8 |

Example 7

Additional Formulations and Vehicles

Additional formulations in accordance with the present description, either containing or lacking an active pharmaceutical ingredient, were made as shown in Table 7.

TABLE 7

| MATERIAL | FUNCTION | Formulation D (% w/w) | Formulation E (% w/w) | Formulation F (% w/w) | Formulation G (% w/w) |
|---|---|---|---|---|---|
| Glycerin | vehicle | 18.405 | | | |
| Ethyl Alcohol | vehicle | 63.04 | 20.00 | 19.85 | |
| Isopropyl Alcohol | vehicle | | | | 54.85 |
| Cyclomethicone | wetting agent | 6.835 | 13.00 | 13.00 | 13.00 |
| Diisopropyl adipate | non-volatile solvent | 6.31 | 12.00 | 12.00 | 12.00 |
| C12-15 alkyl lactate | non-volatile solvent | 5.26 | 10.00 | 10.00 | 10.00 |
| Benzyl Alcohol | vehicle | | 34.85 | | |
| N-methyl-2-pyrrolidone | non-volatile solvent | | | 35.00 | |
| KP-103 | API | 0.00 | 10.00 | 10.00 | 10.00 |
| Vitamin E | anti-oxidant | 0.05 | 0.05 | 0.05 | 0.05 |
| Butylated hydroxytoluene | anti-oxidant | 0.10 | 0.10 | 0.10 | 0.10 |

In contrast to Formulations A-C of Example 5 in which the vehicle is ethyl alcohol, the vehicle of Formulation D is a combination of ethyl alcohol and glycerin, a water-miscible polyol. Formulations E and F contain a low concentration of ethyl alcohol compared to Formulations A-D. In Formulation E, the vehicle is a combination of ethyl alcohol and benzyl alcohol. In Formulation F, the vehicle is ethyl alcohol. In Formulation G, the ethyl alcohol has been replaced with isopropyl alcohol.

Example 8

Determination of Surface Tension of Formulations of Example 7

The surface tensions of Formulations D to G of Example 7 were determined by the method described in Example 6. The surface tension value for each of the formulations is shown below in Table 8.

TABLE 8

| | Formulation | | | |
|---|---|---|---|---|
| | Formulation D | Formulation E | Formulation F | Formulation G |
| Surface Tension (dynes/cm) | 22.4 | 21.6 | 21.7 | 21.7 |

Example 9

Determination of Spreadability

The spreadability of each of Formulations 087 and A to G of Examples 3, 5, and 7 was determined at ambient room temperature of 21° to 25° by utilizing a single glass slide that had been cleaned with isopropyl alcohol and permitted to air dry. 100 microliters of a formulation was placed onto a single point on the cleaned glass slide by positive displacement pipette. The glass slide was placed on graph paper with 0.5 cm×0.5 cm grids to facilitate diameter determinations. The area covered by each of the formulations was essentially circular. The diameter of the spread of the drop was recorded at 1, 2, 4, 6, and 10 minutes. Area was calculated using the following equation. Data is shown in Table 9.

TABLE 9

Covered area $(cm^2) = \pi(d/2)^2 = \pi r^2$
$\pi = 3.141592654$
d = diameter (cm)
r = radius (cm)

| | | Formulations | | | | | | | |
|---|---|---|---|---|---|---|---|---|---|
| | Minutes | 087 | A | B | C | D | E | F | G |
| Single Slide Spreadability Area (cm$^2$) | 1 | 4.9 | 4.9 | 5.9 | 7.1 | 4.0 | 4.9 | 4.9 | 5.9 |
| | 2 | 7.1 | 7.1 | 9.6 | 10.2 | 5.9 | 7.1 | 7.1 | 7.1 |
| | 4 | 9.6 | 9.6 | 15.9 | 15.9 | 14.9 | 12.6 | 12.6 | 8.3 |
| | 6 | 15.9 | 15.9 | 23.8 | 23.8 | 21.6 | 17.7 | 14.2 | 9.6 |
| | 10 | 28.3 | 28.3 | 33.2 | 33.2 | 28.3 | 33.2 | 14.9 | 19.6 |

Each of the tested formulations exhibited a single slide spreadability that continued to increase during the 10 minutes of the test. Further, each of the tested formulations had a spreadability area of at least 14.0 cm$^2$ within 10 minutes.

Example 10

Additional Formulations (Prior Art)

Additional formulations H and I, not in accordance with the present description, were made as shown in Table 10. Formulation H is 100% water and Formulation I is a combination of 63% ethyl alcohol and 37% octocrylene. An additional formulation was Formulation J which is a commercially available PENLAC® NAIL LACQUER (ciclopirox) 8% Topical Solution (Dermik Laboratories, Bridgewater, N.J.). An additional formulation was Formulation K which is a commercially marketed LOCERYL® NAIL LACQUER (amorolfine) (Galderma Australia), currently marketed in countries other than the United States. Prior art formulations J and K contain film forming polymeric agents and form a lacquer upon application to the surface of a nail.

Example 11

Determination of Surface Tension of Formulations of Example 10

The surface tensions of Formulations H to K of Example 10 were determined by the method described in Example 6. The surface tension value for each of the formulations is shown below in Table 10.

TABLE 10

| | Formulation | | | |
|---|---|---|---|---|
| | H | I | J | K |
| Surface Tension (dynes/cm) | 72.5 | 24.6 | 22.7 | 23.7 |

Example 12

Determination of Spreadability of Formulations of Example 10

The spreadability of Formulations H to K of Example 10 was determined by the method described in Example 9. Data is shown in Table 11.

TABLE 11

| | | Formulations | | | |
|---|---|---|---|---|---|
| | Minutes | H | I | J | K |
| Single Slide Spreadability Area (cm$^2$) | 1 | 1.2 | 14.2 | 1.4 | 4.0 |
| | 2 | 1.2 | 14.2 | 1.4 | 4.0 |
| | 4 | 1.2 | 14.2 | 1.4 | 4.0 |
| | 6 | 1.2 | 14.2 | 1.4 | 4.0 |
| | 10 | 1.2 | 14.2 | 1.4 | 4.0 |

Formulations H and I are controls that consist of water and two vehicles, respectively. Prior art formulations J and K contain film forming polymeric compounds. As shown in Examples 11 and 12, Formulations H to K are not suitable for the present composition and method.

Example 13

Determination of Surface Tension and Spreadability of Formulation of the Invention without Active Ingredients Table 12 shows a formulations of the present invention, but lacking an active pharmaceutical ingredient, that was made and tested for surface tension as described in Example 6 and for spreadability as described in Example 9. Although this formulation lacks an API, it represents an example of the formulation of the invention upon the inclusion of an API.

TABLE 12

| Material | Primary Function | Formulation L (% w/w) |
|---|---|---|
| Alcohol | Vehicle | 63.04 |
| Cyclomethicone | Wetting Agent | 13.67 |
| Diisopropyl Adipate | Nonvolatile Solvent | 12.62 |
| C12-15 Alkyl Lactate | Nonvolatile Solvent | 10.52 |
| Vitamin E | Antioxidant | 0.05 |
| BHT | Antioxidant | 0.1 |
| Tests Performed | | |
| Surface Tension (dynes/cm) | | 21.8 |
| Spreadability at 10 minutes (cm$^2$) | | 33.2 |

Example 14

Formulations Including an API.s

The following examples in Table 13 represent formulations of the invention that include representative APIs to illustrate the versatility and utility of low surface tension formulations for improved efficacy in the topical treatment of nail disease.

clear nail. The frequency of clinical success calculated as complete cure and almost clear is summarized in Table 14.

TABLE 13

| Material | Primary Function | Formulation M (% w/w) | Formulation N (% w/w) | Formulation O (% w/w) | Formulation P (% w/w) | Formulation Q (% w/w) |
|---|---|---|---|---|---|---|
| Ciclopirox | Antifungal | 8.0 | — | — | — | — |
| Halobetasol Propionate | Corticosteroid | — | — | — | 0.05 | — |
| Urea | Keratolytic | — | — | 30.0 | — | — |
| Erythromycin | Antibiotic | — | 2.0 | — | — | — |
| KP-103 | Antifungal | — | — | — | — | 10.0 |
| Alcohol | Vehicle | 61.4 | 67.5 | — | 64.95 | 54.85 |
| Purified Water | Vehicle | 5.0 | 5.0 | 53.0 | — | — |
| Hexylene Glycol | Vehicle | 25.0 | 25.0 | — | — | — |
| Propylene Glycol | Vehicle | — | — | 15.0 | — | — |
| Sodium Lauryl Sulfate | Wetting Agent | 0.5 | 0.5 | 2.0 | — | — |
| Cyclomethicone | Wetting Agent | — | — | — | 13.0 | 13.0 |
| Diisopropyl Adipate | Nonvolatile Solvent | — | — | — | 12.0 | 12.0 |
| C12-15 Alkyl Lactate | Nonvolatile Solvent | — | — | — | 10.0 | 10.0 |
| Vitamin E | Antioxidant | — | — | — | — | 0.05 |
| BHT | Antioxidant | 0.1 | — | — | — | 0.1 |

One general method for making the compositions in Table 13 is as follows. For lipophilic APIs such as halobetasol propionate and KP-103, the API is first dissolved n alcohol with propeller mixing, followed by the addition and dissolution of the antioxidants, if any. Next a wetting agent is added with continued mixing. Finally one or more non-volatile solvents are added to the formulation.

For the lipophilic APIs erythromycin and ciclopirox, a wetting agent is dissolved in the water with propeller mixing. This mixture is added to hexylene glycol with mixing. Next the alcohol is added. The API along with the antioxidant, if any, is then added to the mixture and which is mixed until the API is dissolved using propeller mixing. For the hydrophilic API urea, the sodium lauryl sulfate is dissolved in water with propeller mixing. The API is added next with continued mixing until dissolved. Finally the propylene glycol is added and mixed. The last step for all compositions is packaging in tightly-closed pharmaceutically acceptable containers.

Example 15

Clinical Efficacy in Onychomycosis

The composition of Example 14, formula Q, containing 10% KP-103, was evaluated in a double-blind vehicle-controlled parallel-group clinical study for the treatment of toenail onychomycosis. Efficacy was assessed by an investigator 40 weeks after the start of treatment based on a designated great toenail with average disease involvement of 40% (range 20 to 90%) at the beginning of the study. Patients made once daily applications of the test composition or the vehicle (same composition with active agent KP-103 replaced with alcohol) to the affected toenails for 36 weeks, with efficacy assessments being made at the follow-up visit 4 weeks later. Complete cure was defined as clear nail (no disease involvement) plus negative mycology. Almost clear was defined as negative mycology plus clear nail or growth of 3 mm or more of new clear nail. The frequency of clinical success calculated as complete cure and almost clear is summarized in Table 14.

TABLE 14

| Parameter | KP-103, 10% | Vehicle (no API) |
|---|---|---|
| Number of Subjects | 39 | 22 |
| Complete Cure - Number | 10 | 2 |
| Complete Cure - Percent | 25.6 | 9.1 |
| Almost Clear - Number | 25 | 5 |
| Almost Clear - Percent | 64.1% | 22.7% |

Table 14 shows that the formulation of the invention provided an efficacy much higher than that obtained by presently available topical formulations. The present formulation provided a success rate that is dramatically higher than that obtained by present topical and even some systemic methods of treatment of onychomycosis. The present formulation provided three and a half times more complete cures than reported for Penlac Nail Lacquer and from 0.66 to 1.8 times the complete cures reported for itraconazole and terbinafine, respectively, two orally administered antifungal drugs approved in the USA for treatment of onychomycosis.

While preferred embodiments of the invention have been described in detail, it will be apparent to those skilled in the art that the disclosed embodiments may be modified. It is intended that such modifications be encompassed in the following claims. Therefore, the foregoing description is to be considered to be exemplary rather than limiting, and the scope of the invention is that defined by the following claims.

The invention claimed is:

1. A pharmaceutical composition consisting essentially of a vehicle that is volatile and/or that rapidly penetrates a nail following application onto the surface of the nail, a triazole antifungal active pharmaceutical ingredient (API), and a wetting agent, and optionally a non-volatile solvent that is dissolved, suspended, dispersed, or emulsified within the vehicle, wherein the surface tension of the composition is 40 dynes/cm or less and wherein the composition, when applied to the surface of a nail, does not form a solid film.

2. The pharmaceutical composition for the topical treatment of a disorder of the nail or nail bed of claim 1 wherein the vehicle is alcohol and the wetting agent is a volatile silicone, and wherein the composition contains a non-volatile solvent that is dissolved, suspended, dispersed, or emulsified within the vehicle wherein the non-volatile solvent is one or more esters of the formula RCO—OR', wherein R and R' may be identical or different and each of R and R' represents a linear or branched chain of an alkyl, alkenyl, alkoxycarbonylalkyl, or alkoxycarbonyloxyalkyl radical having from 1 to 25 carbon atoms, and wherein the chain of R' is at least 5 carbons, wherein the volatile silicone is present in the composition at a concentration less than 25% w/w.

3. The pharmaceutical composition of claim 2 wherein the ester is a combination of diisopropyl adipate and C12-15 alkyl lactate.

4. The pharmaceutical composition of claim 2 wherein the ester is a combination of diisopropyl adipate and myristyl lactate.

5. The pharmaceutical composition of claim 2 wherein the triazole antifungal agent is (2R,3R)-2-(2,4-difluorophenyl)-3-(4-methylenepiperidine-1-yl)-1-(1H-1,2,4-triazole-1-yl)butane-2-ol.

6. The pharmaceutical composition of claim 2 wherein the alcohol is ethanol.

7. The pharmaceutical composition of claim 2 wherein the volatile silicone is a cyclic silicone.

8. The pharmaceutical composition of claim 7 wherein the cyclic silicone is a cyclomethicone.

9. The pharmaceutical composition of claim 2 wherein the concentration of volatile silicone is less than 20%.

10. The pharmaceutical composition of claim 2 wherein the concentration of volatile silicone is less than 15%.

11. The pharmaceutical composition of claim 1 that consists essentially of alcohol, cyclomethicone, diisopropyl adipate, either or both of C12-15 alkyl lactate and isopropyl myristate, and a triazole antifungal agent.

12. The pharmaceutical composition of claim 11 that consists essentially of the following components in the following ranges of concentrations % w/w:
   a. alcohol—10% to 80%
   b. cyclomethicone—0.01% to less than 25%
   c. diisopropyl adipate plus either or both of C12-15 alkyl lactate and isopropyl myristate—5% to 90%
   d. triazole antifungal agent—0.0001% to 30%.

13. The pharmaceutical composition of claim 12 that consists essentially of:
   a. alcohol—50% to 70%,
   b. cyclomethicone—10% to 15%
   c. diisopropyl adipate—8% to 15%
   d. either or both of C12-15 alkyl lactate and isopropyl myristate—8% to 15%
   e. triazole antifungal agent—2% to 15%.

14. The pharmaceutical composition of claim 13 wherein the triazole antifungal agent is (2R,3R)-2-(2,4-difluorophenyl)-3-(4-methylenepiperidine-1-yl)-1-(1H-1,2,4-triazole-1-yl)butane-2-ol.

15. The pharmaceutical composition of claim 2 wherein the composition does not include a polymeric film forming compound.

16. The pharmaceutical composition of claim 2 which increases in spread on the surface of a clean dry glass slide throughout the six-minute period immediately following application of the composition to the surface of the slide.

17. The pharmaceutical composition of claim 16 wherein the spread of the composition on the surface of the slide encompasses an area of greater than 11.0 cm within 10 minutes following application of 100 microliters of the composition to the surface of the slide.

18. The pharmaceutical composition of claim 2 wherein the surface tension of the composition is 35 dynes/cm or less.

19. The pharmaceutical composition of claim 18 wherein the surface tension of the composition is 30 dynes/cm or less.

20. The pharmaceutical composition of claim 18 wherein the surface tension of the composition is 25 dynes/cm or less.

21. The pharmaceutical composition for the topical treatment of a disorder of the nail or nail bed of claim 1 which consists essentially of a volatile alcohol, a volatile silicone, one or more esters of the formula RCO—OR', wherein R and R' may be identical or different and each of R and R' represents a linear or branched chain of an alkyl, alkenyl, alkoxycarbonylalkyl, or alkoxycarbonyloxyalkyl radical having from 1 to 25 carbon atoms, and wherein the chain of R' is at least 5 carbons, and a triazole antifungal agent, wherein the ratio of alcohol to volatile silicone in the composition % w/w is at least 2:3.

22. The pharmaceutical composition of claim 21 wherein the ester is combination of diisopropyl adipate and C12-15 alkyl lactate.

23. The pharmaceutical composition of claim 21 wherein the ester is a combination of diisopropyl adipate and myristyl lactate.

24. The pharmaceutical composition of claim 21 wherein the triazole antifungal agent is (2R,3R)-2-(2,4-difluorophenyl)-3-(4-methylenepiperidine-1-yl)-1-(1H-1,2,4-triazole-1-yl)butane-2-ol.

25. The pharmaceutical composition of claim 21 wherein the alcohol is ethanol.

26. The pharmaceutical composition of claim 21 wherein the volatile silicone is a cyclic silicone.

27. The pharmaceutical composition of claim 21 wherein the cyclic silicone is a cyclomethicone.

28. The pharmaceutical composition of claim 21 wherein the ratio of alcohol to volatile silicone is at least 1:1.

29. The pharmaceutical composition of claim 21 wherein the ratio of alcohol to volatile silicone is at least 2:1.

30. The pharmaceutical composition of claim 21 wherein the ratio of alcohol to volatile silicone is at least 3:1.

31. The pharmaceutical composition of claim 21 wherein the composition does not include a polymeric film forming compound.

32. The pharmaceutical composition of claim 21 which increases in spread on the surface of a clean dry glass slide throughout the six-minute period immediately following application of the composition to the surface of the slide.

33. The pharmaceutical composition of claim 21 wherein the spread of the composition on the surface of the slide encompasses an area of greater than 11.0 cm within 10 minutes following application of 100 microliters of the composition to the surface of the slide.

34. The pharmaceutical composition of claim 21 that consists essentially of alcohol, cyclomethicone, diisopropyl adipate, either or both of C12-15 alkyl lactate and isopropyl myristate, and a triazole antifungal agent.

35. The pharmaceutical composition of claim 34 that consist essentially of the following components in the following ranges of concentrations % w/w:
   a. alcohol—10% to 80%
   b. cyclomethicone—0.01% to less than 25%
   c. diisopropyl adipate plus either or both of C12-15 alkyl lactate and is isopropyl myristate—5% to 90%
   d. triazole antifungal agent—0.0001% to 30%.

36. The pharmaceutical composition of claim 35 that consists essentially of:
   a. alcohol—50% to 70%,
   b. cyclomethicone—10% to 15%
   c. diisopropyl adipate—8% to 15% d. either or both of C12-15 alkyl lactate and isopropyl myristate—8% to 15% e. triazole antifungal agent—2% to 15%.

37. The pharmaceutical composition of claim 36 wherein the triazole antifungal agent is (2R,3R)-2-(2,4-difluorophenyl)-3-(4-methylenepiperidine-1-yl)-1-(1H-1,2,4-triazole-1-yl)butane-2-ol.

38. The pharmaceutical composition of claim 21 wherein the surface tension of the composition is 35 dynes/cm or less.

39. The pharmaceutical composition of claim 38 wherein the surface tension of the composition is 30 dynes/cm or less.

40. The pharmaceutical composition of claim 39 wherein the surface tension of the composition is 25 dynes/cm or less.

41. A pharmaceutical composition consisting essentially of a vehicle that is volatile and/or that rapidly penetrates a nail following application onto the surface of the nail, an antifungal active ingredient (2R,3R)-2-(2,4-difluorophenyl)-3-(4-methylenepiperidine-1-yl)-1-(1H-1,2,4-triazole-1-yl)butane-2-ol, and a wetting agent, and optionally a non-volatile solvent that is dissolved, suspended, dispersed, or emulsified within the vehicle, wherein the surface tension of the composition is 40 dynes/cm or less and wherein the composition, when applied to the surface of a nail, does not form a solid film.

42. The pharmaceutical composition of claim 41 that does not include a polymeric film forming compound.

\* \* \* \* \*